United States Patent [19]
Holdsworth et al.

[11] Patent Number: 5,485,831
[45] Date of Patent: Jan. 23, 1996

[54] PULSE-INJECTOR FOR QUANTITATIVE ANGIOGRAPHIC BLOOD-FLOW MEASUREMENTS

[75] Inventors: David W. Holdsworth; Maria Drangova; Aaron Fenster, all of London, Canada

[73] Assignee: University Hospital (London) Development Corporation, Ontario, Canada

[21] Appl. No.: 159,166

[22] Filed: Nov. 30, 1993

[30] Foreign Application Priority Data

Nov. 30, 1992 [GB] United Kingdom ............... 9225014

[51] Int. Cl.[6] .................................................. A61M 25/00
[52] U.S. Cl. ..................... 128/654; 128/655; 128/658; 604/32
[58] Field of Search ..................... 128/654, 655, 128/656, 658, DIG. 6, DIG. 12, DIG. 13; 604/32

[56] References Cited

U.S. PATENT DOCUMENTS

| | | | |
|---|---|---|---|
| 3,086,525 | 4/1963 | Whitcomb | 128/658 |
| 3,785,683 | 1/1974 | Adelhed | 128/654 |
| 3,828,767 | 8/1974 | Spiroff | 128/658 |
| 3,859,985 | 1/1975 | Eckhart | 604/32 |
| 4,006,736 | 2/1977 | Kranys et al. | 128/655 |
| 4,279,252 | 7/1981 | Martin | 128/658 |
| 4,562,829 | 1/1986 | Bergner | 128/655 |
| 4,737,153 | 4/1988 | Shimamura et al. | 128/658 |
| 4,784,984 | 6/1988 | Patel | 128/658 |
| 5,024,230 | 6/1991 | Lindstrom et al. | 128/654 |
| 5,037,403 | 8/1991 | Garcia | 128/658 |
| 5,147,334 | 9/1992 | Moss | 128/658 |
| 5,163,431 | 11/1992 | Griep | 128/658 |
| 5,300,048 | 4/1994 | Drewes, Jr. et al. | 128/658 |
| 5,322,070 | 6/1994 | Goodman et al. | 128/654 |

*Primary Examiner*—Krista M. Zele
*Attorney, Agent, or Firm*—Keck, Mahin & Cate

[57] ABSTRACT

A technique for pulsed-injection of radiographic contrast agent uses a pressurized source of contrast agent interrupted by a rotary valve at rates ranging from 1 to 30 Hz. This produces well-defined boli at the end of the catheter. The position of these boli is recorded by a digital radiographic system and analyzed to produce quantitative measurements of blood velocity and flow rate throughout the cardiac cycle.

35 Claims, 5 Drawing Sheets

PULSE-INJECTOR FOR QUANTITATIVE ANGIOGRAPHIC BLOOD-FLOW MEASUREMENTS

Clinical measurements of arterial blood flow are used for both diagnosis of disease severity and for assessing the success of interventional and surgical procedures. Both the average flow rate and the degree of waveform pulsatility are of clinical interest. Because of this interest, several techniques have been developed to measure blood flow and velocity using Doppler ultrasound and magnetic resonance imaging. Although these techniques show great promise, they have yet to displace conventional x-ray angiographic techniques in clinical practice, although they may be used in addition to x-ray angiography to assess stenosis severity.

X-ray angiographic procedures still remain the "gold standard" for determining anatomical information, such as lumen boundary. Since angiography is in common clinical use, there has been considerable interest in the development of x-ray techniques to measure blood-flow rate. Quantitative angiographic flow measurements have the potential to provide additional functional information with little additional risk to the patient.

Previous x-ray angiographic techniques to measure blood flow have involved the injection of iodinated contrast agent while recording the passage of the bolus through the vessel of interest, usually with digital-subtraction angiography (DSA) at the highest frame rate possible. The resulting image sequence can then be processed by one of several quantitative techniques which analyze the passage of contrast agent through the vessel. These techniques include analysis of the dilution curve by Stewart-Hamilton's formula, transit-time analysis, and cross-correlation techniques, including statistical cross-correlation.

Pulsed-injection of contrast agent has been proposed to improve the accuracy and precision of quantitative radiographic flow measurement techniques. Pulsed injection with multiple boll provides an improved signal, since more features are presented within the vessel, for the same volume of injected contrast agent. Techniques have been developed using a pulsed-injector system which showed promising results in vitro tests. However, an injector with improved bolus definition at high pulsing speeds is required to measure the entire range of flow rates found in the vasculature.

According to the present invention, there is provided apparatus supplying a pressurized source of contrast agent to a vessel and a control valve to control flow of the agent from the source into the vessel. The control valve is a rotary valve that aligns a supply port with an outlet port as the body of the valve rotates. Flow to the vessel is thus pulsed. The resulting distribution of contrast agent within the vessel provides a strong radiographic signal for quantitative flow and velocity analysis, using techniques such as cross-correlation.

An embodiment of the invention will now be described with reference to the accompanying drawings, in which FIG. 1 shows a schematic diagram of the pulsed injector system;

Figure 1:
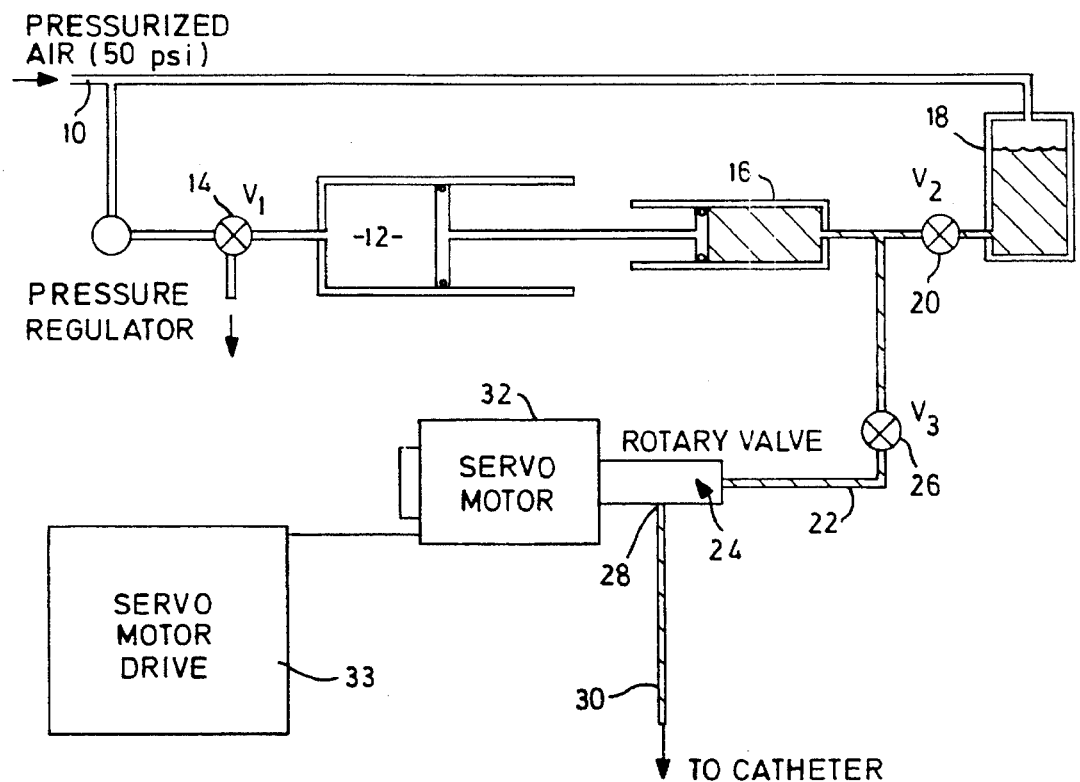

Referring to FIG. 1, a pressurized air supply 10 is regulated over the range 40 to 100 Kpa and introduced into a low-pressure cylinder 12 through valve 14. The low-pressure cylinder 12 (inside diameter 38 mm) drives a piston in the high-pressure cylinder 16 (inside diameter 9.8 mm), resulting in a factor of 15 increase in pressure. This allows the production of the high pressures needed to drive contrast agent through small diameter catheters, while retaining compatibility with low-pressure medical air sources commonly found in a hospital environment. Air supply 12 is also connected to a heated reservoir 18 of contrast agent that supplies the cylinder 16 through a valve 20.

The high pressure cylinder 16 is connected by a supply duct 22 with a rotary valve 24 described in further detail below. Flow between the cylinder 16 and valve 24 is controlled by a valve 26. When the valve 26 is opened, the high-pressure cylinder drives contrast agent through supply duct 22 to rotary valve 24 to produce a series of pulses of contrast agent at an outlet 28 connected to a catheter 30. When the high-pressure cylinder has been emptied of contrast agent, it is refilled quickly by closing valve 26, opening valve 20, and venting valve 14 to atmospheric pressure. This sequence of operations causes 10 ml of pre-heated contrast agent to flow from the reservoir 18 into the high-pressure cylinder 16, in preparation for the next injection sequence.

Figure 2:
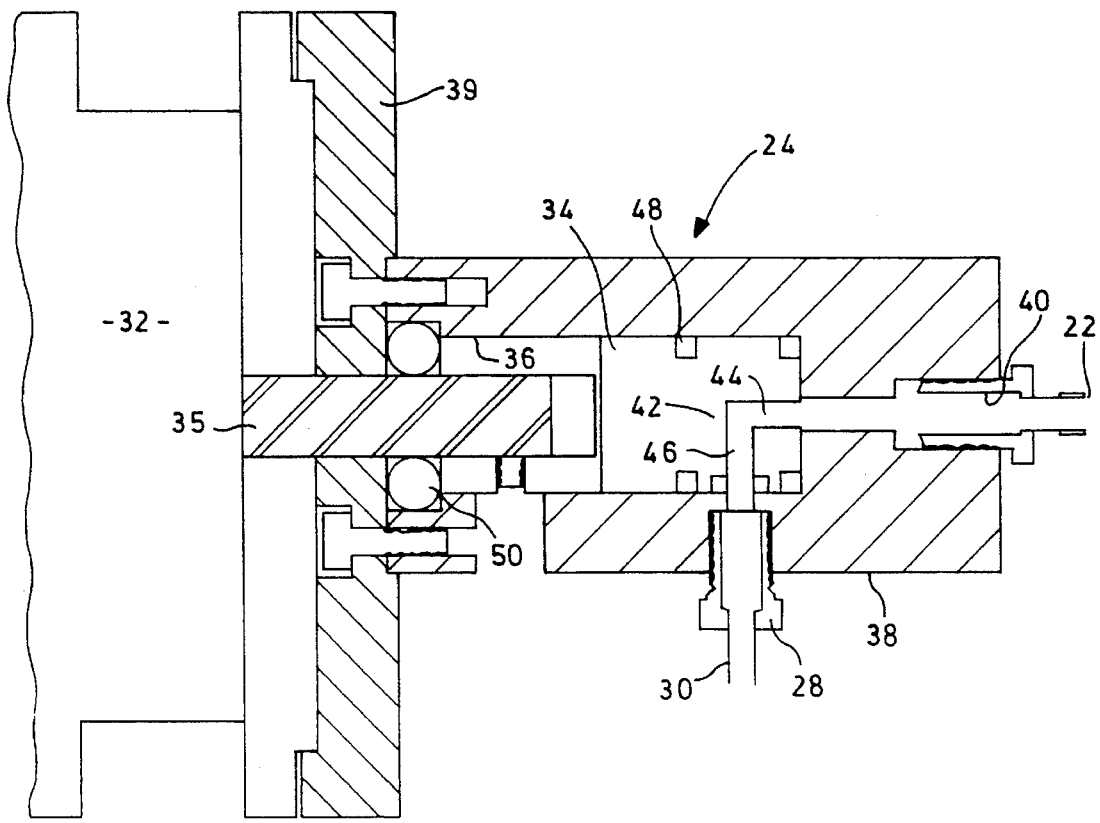
FIG. 2 shows on an enlarged scale a section of a rotary valve shown in FIG. 1.

The rotary valve 24 is shown in more detail in FIG. 2. Valve 24 is driven by a DC servo-motor 32 under the control of a servo drive 33. The motor 32 includes a driveshaft 35 connected to a cylindrical teflon valve body 34. Body 34 is rotatably mounted within a cylindrical bore 36 provided in a brass housing 38 that is connected through base plate 39 to the motor 32 so as to allow relative rotation between the valve body 34 and housing 38. The servo drive 33 is operable to control the rotational speed of the motor 32 in a conventional manner.

Supply duct 22 is connected to an end port 40 located in the housing on the axis of rotation of the valve body 34. An internal passageway 42 is provided in the valve body 34 and has an axial leg 44 aligned with end port 40 and a radial leg 46. The radial leg 46 is axially located to be aligned with outlet 28 in the housing 38 which is connected to catheter 30.

As the valve body 24 rotates, the radial leg 46 comes periodically into alignment with the outlet 28 of the housing 38 and contrast agent is able to flow through the valve 24 from port 40 to outlet 28. At other times during the rotation of the valve body 34, the housing 38 blocks flow through the duct 42 and prevents flow out of the outlet 28. The duty cycle of the valve 24, i.e. the fraction of each cycle that the valve is open, is thus determined by the diameter of the radial leg 46 and the circumference of the body 34. In a preferred design, the body circumference is 80 mm and the radial leg diameter is 3.2 mm, resulting in a duty cycle of 8%. O-ring seals 48 are provided on the valve body 34 to prevent contrast agent from leaking past the valve body 34 and thrust bearings 50 are located between the base plate 39 and the body 34 to prevent excessive thrust loads on the DC servo-motor 32.

Figure 3:
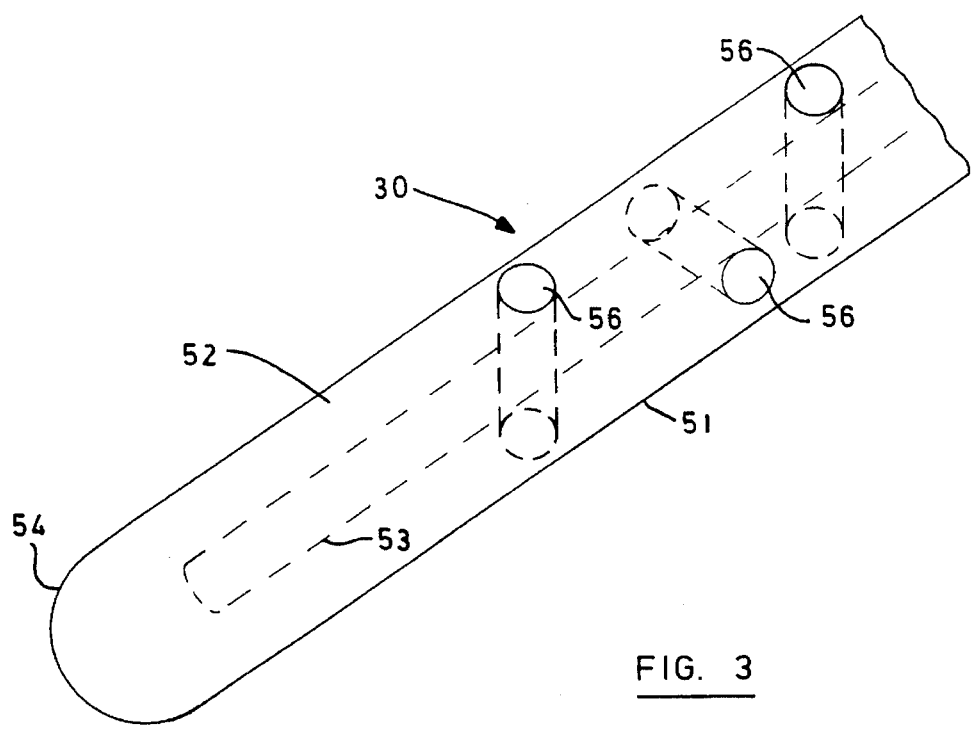
FIG. 3 shows a perspective view of a catheter used with the apparatus of FIG. 1.

The objective of the pulsed-injection technique is to produce compact boli of contrast agent within the vessel. Thus, it is important that the contrast agent not be spread excessively along the vessel when it is ejected from the catheter 30. Catheter 30 includes an elongate body 51 with an internal duct 53. The tip 52 of catheter 30 as shown in FIG. 3 has been found to provide a reduced dispersal of contrast agent. The end face 54 of the tip 52 of the catheter 30 is sealed so as to be leak-tight. Three pairs of apertures 56 are formed in the wall of the catheter 30 to provide a total of six apertures. Each pair of apertures 56 is axially and circumferentially spaced from the adjacent pair so that two pairs are aligned on the diameter of the catheter and the intermediate pair is disposed at 90° to the other two. It has been found that an aperture diameter of 0.7 mm and an axial spacing of 2 mm between adjacent pairs of apertures has been appropriate with a catheter having an internal duct with a diameter of 1 mm. This hole pattern not only produces an exit orifice with a total area which is three times larger than that obtained with an end-hole alone but also reduces the initial extent of the bolus along the vessel to less than 1 cm in length. The increased exit area also avoids jetting of the agent and consequent impingement against the side wall of the vessel.

Figure 4:
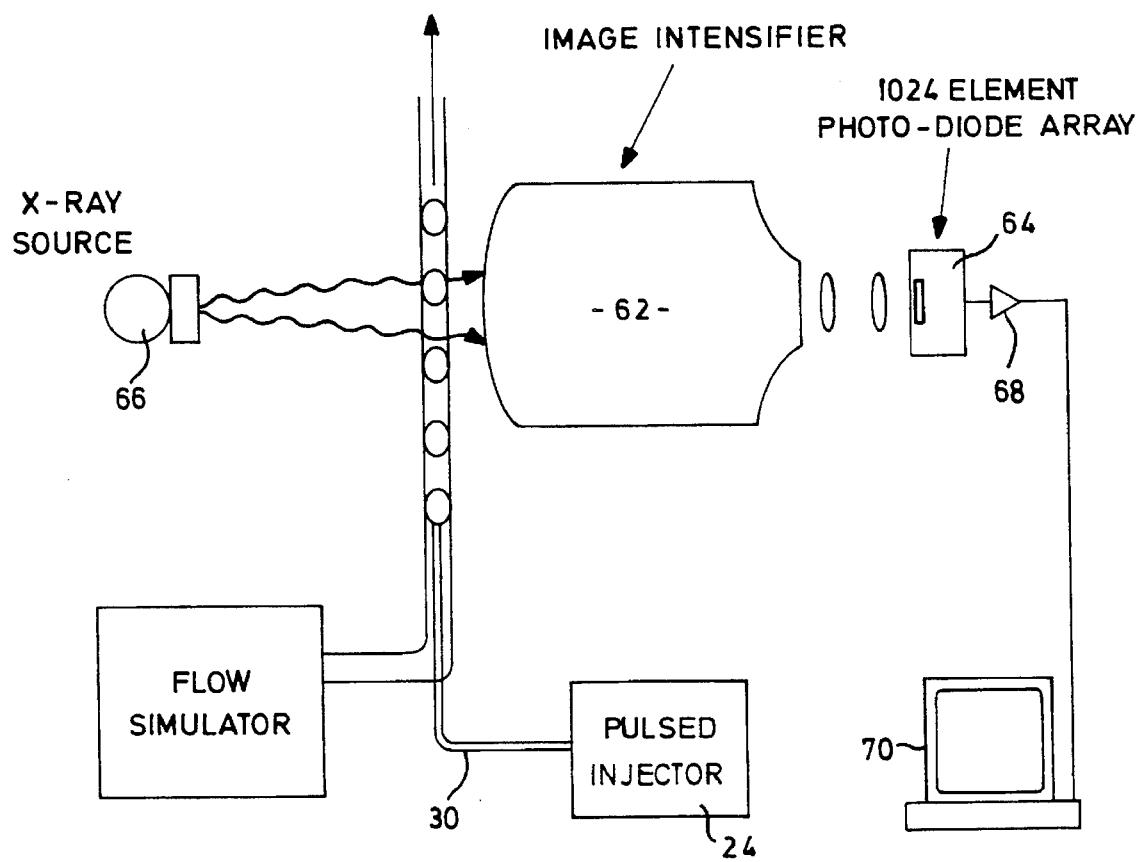
FIG. 4 shows the use of the apparatus of FIG. 1 in the collection of data.

To verify the performance of the pulsed injector with a digital angiographic system, tests were performed in vitro with an x-ray image intensifier (XRII) 62 coupled to a linear photodiode array (PDA) 64 as shown schematically in FIG. 4. X-rays from source 66 pass through the vessel of interest and are detected by the XRII 62 after processing by image intensifier 62. The optical output signal from the XRII 62 is transferred to a 1024 element PDA 64 (Reticon RL 1024S). The PDA 64 is positioned such that its long axis is aligned with the long axis of the vessel of interest, and magnification factors are chosen such that the entire diameter of the vessel is recorded by the PDA 64. In this manner, the PDA 64 provides instantaneous integration of the signal across the vessel diameter, with the PDA elements recording this information at each of 1024 points along the vessel simultaneously. The output from the PDA 64 is digitized with a 12-bit ADC 68 at a line rate of 60 Hz. Thus, a distance-density curve was recorded by the acquisition computer 70 every 16.6 ms, for a total acquisition time of up to 8 s.

Simulated blood flow for the in vitro experiments has been provided by a computer-controlled flow simulator which consists of a piston driven within a 450 ml glass housing by a micro-stepping motor. This produces steady and pulsatile flow waveforms to within ±1%, with waveform shape specified completely from flow-rate values tabulated in a data file. Such a device is described more fully in an article entitled "Computer Controlled Positive Displacement Pump for Physiological Flow Simulation" by D. W. Holdsworth et al. published in Med. Bio. Eng. & Computing, Vol. 29, at pages 565–570 (1991). For the in vitro experiments described below, the simulator was used to produce steady flow over the range of 5 to 30 ml s$^{-1}$, as well as simulated human carotid and femoral flow waveforms.

Figure 5:
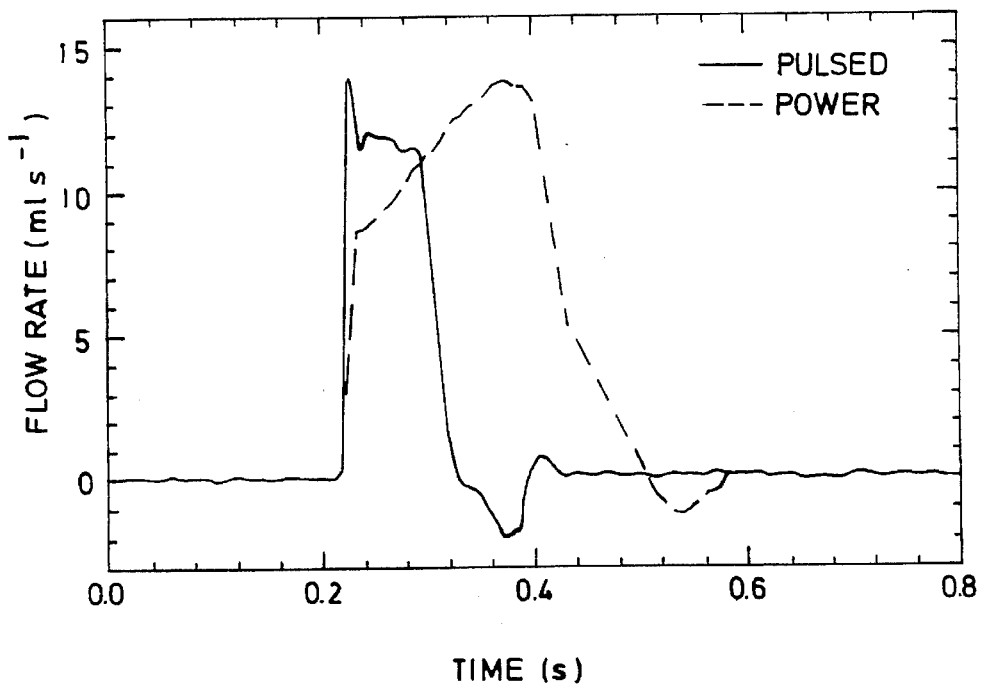
FIG. 5 shows the change of flow rate at the output from the valve in FIG. 2 compared with a commercially available valve.

As noted above, rotation of the valve body 34 within housing 38 produces a pulsed flow of agent at the output 28. FIG. 5 shows the form of the pulse produced as flow rate versus time from which it can be seen that sharp (vertical) leading and trailing edges are produced. By comparison, a pulse form produced by a commercially available unit available from Viamonte-Hobbs under model number 2000 is shown in chain dot line on FIG. 5.

Figure 6:
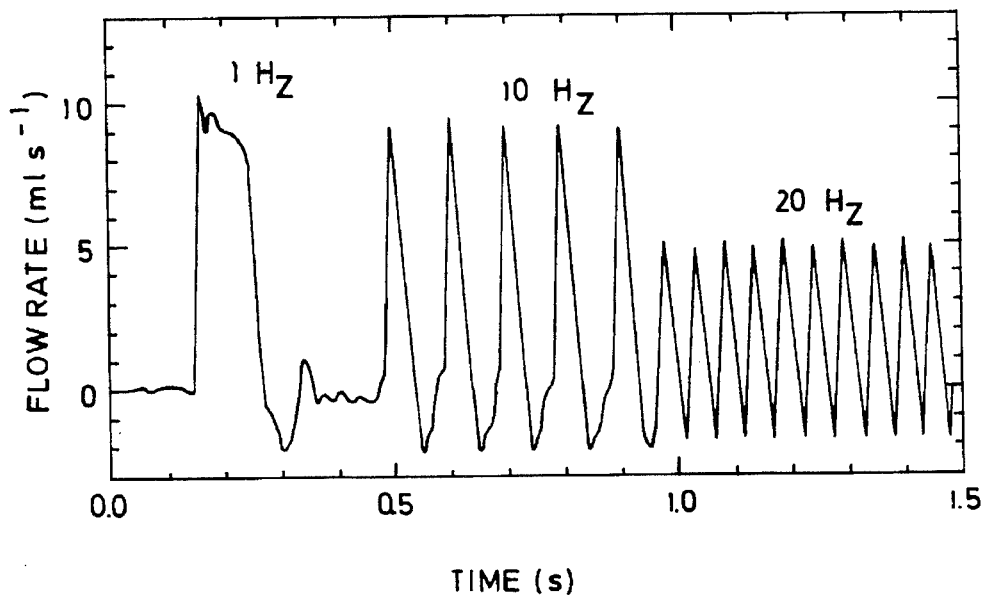
FIG. 6 shows the change of flow rate of the contrasting agent at the outlet to the valve in FIG. 2 for varying operating frequencies.

FIG. 6 shows the pulse forms as the rotational speed of the body 34 within housing 36 is increased under the control of servo drive 33. As can be seen, the leading and trailing edges remain well defined with a reduction in the maximum flow rate as the frequency, i.e. the rotational speed, increases.

Figure 7:
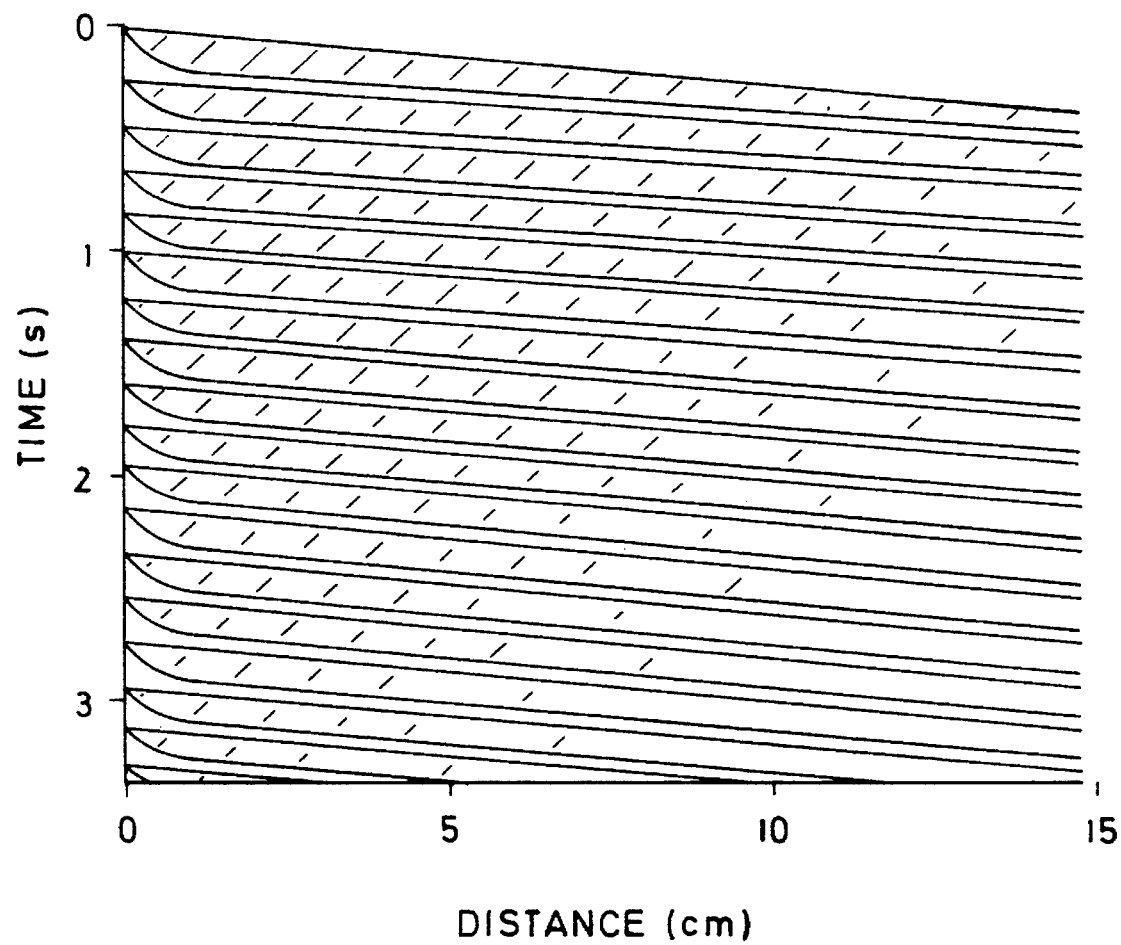
FIG. 7 shows a sample image obtained from the apparatus of FIG. 4.

A typical set of results from the apparatus of FIG. 4 is shown in FIG. 7 with the passage of a bolus of agent along the vessel being identified as dark (x-ray absorbing) streaks proceeding from left to right. The slope of the streaks represents the velocity of flow in the vessel. The high definition of the pulses produced by the valve 24 enhances the definition of the passage of the bolus on the image shown in FIG. 7.

Figure 8:
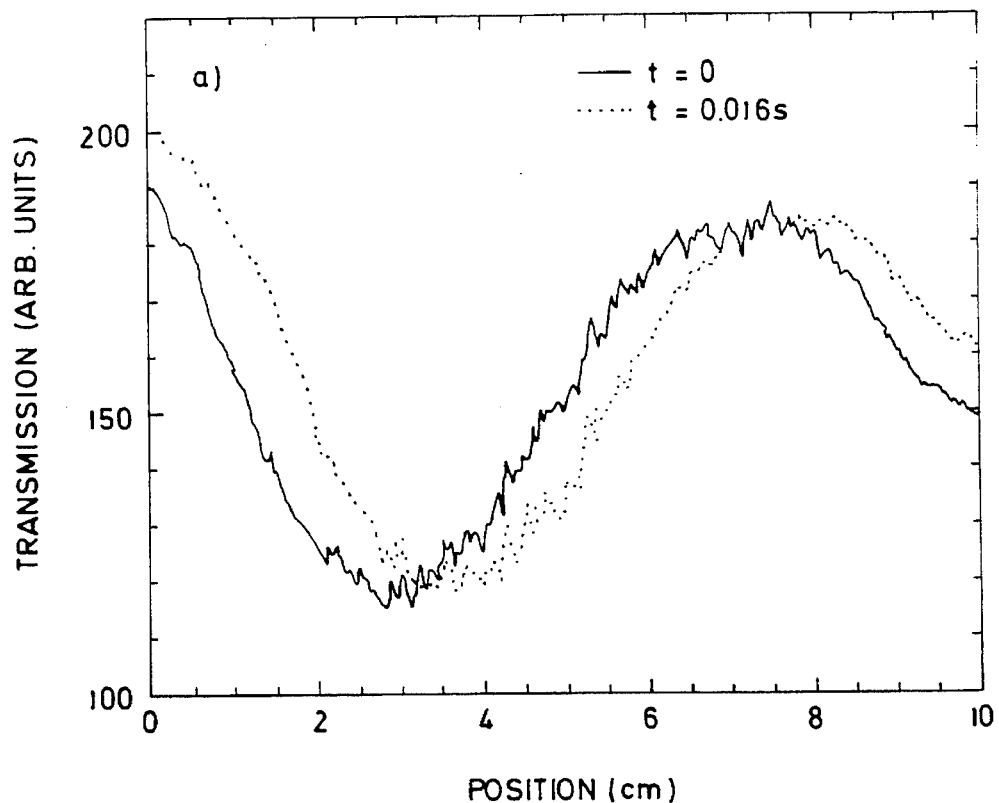
FIG. 8 shows the passage of a bolus of agent along a vessel.
Figure 9:
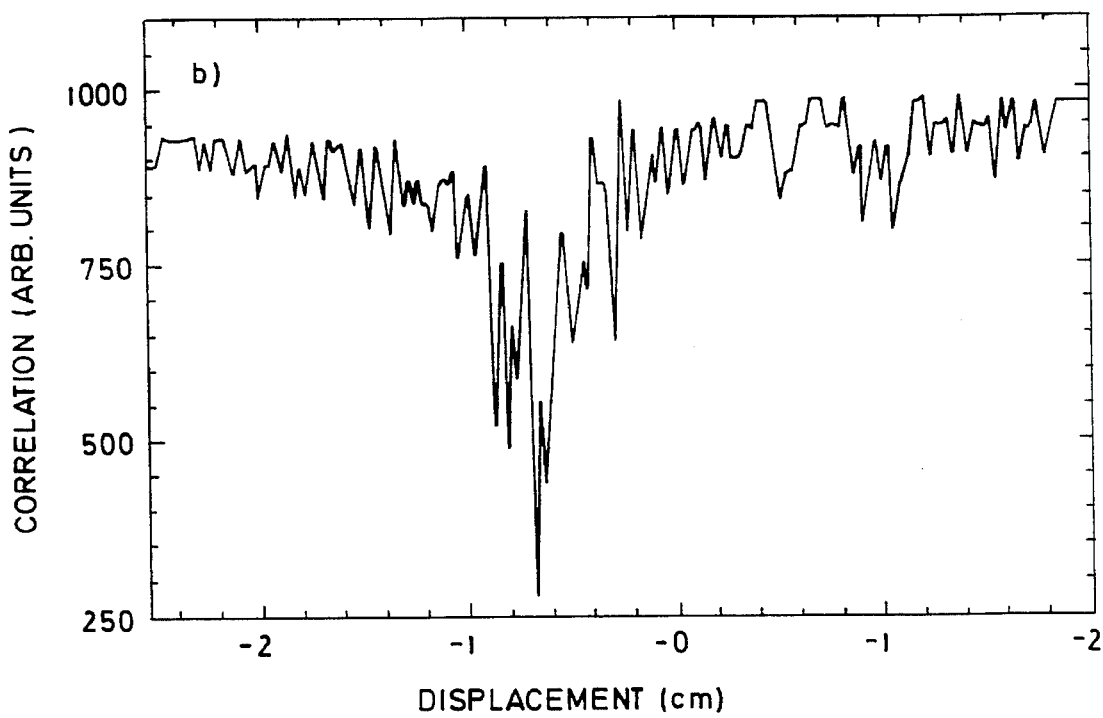
FIG. 9 shows the results obtained by correlating successive values of the curve of FIG. 8.

A further representation of the passage of the bolus along the vessel is shown in FIG. 8 which represents a plot of transmission through the vessel versus position along the vessel at different times. Traces obtained at different times are indicated by different line formats. It can be seen that the minimum transmission, corresponding to the bolus position, is well defined and progressively moves along the vessel. The enhanced definition of the bolus produced by the valve 24 and catheter 30 is clearly seen from the correlation of the results of FIG. 8 represented on the curve of FIG. 9 with a well defined minimum value displaced from the origin by a distance equivalent to movement of the bolus through the vessel in the interval between the correlated samples. This provides an indication of the average velocity of fluid at a given location of the vessel. Flow rate can then be determined if the cross-sectional area of the vessel is known.

We claim:

1. Injection apparatus for quantitative angiographic blood flow measurements by injection of a contrast agent into a fluid transporting vessel, said apparatus comprising a pressurized source of contrast agent, a catheter for conducting the contrast agent from the source into the vessel, a control valve to control flow of said agent between said source and said vessel, said control valve having an inlet port connected to said source, an outlet port connected to said catheter and a valve body within a housing and including a passageway to extend between said inlet and outlet port, said valve body being rotatable within said housing between an open position in which flow between said inlet and said outlet is permitted and a closed position in which flow between said inlet and said outlet is inhibited to connect and disconnect periodically said inlet port and said outlet port and thereby alternately allow and inhibit fluid flow therebetween.

2. Injection apparatus according to claim 1 wherein said body includes a circumferential surface and said passageway includes a radial portion intersecting said surface and alignable with one of said ports during rotation of said body.

3. Injection apparatus according to claim 2 wherein said passageway includes an axial portion extending from said radial portion to another of said ports.

4. Injection apparatus according to claim 3 wherein said axial portion is located on the axis of rotation of said body.

5. Injection apparatus according to claim 4 wherein said axial portion is connected to said inlet port.

6. Injection apparatus according to claim 5 wherein said outlet port is located in a circumferential wall of said housing extending about said circumferential wall of said valve body and axially aligned with said radial portion.

7. Injection apparatus according to claim 1 wherein a drive motor is connected to said valve body to effect rotation thereof.

8. Injection apparatus according to claim 7 including a controller to vary the speed of rotation of said motor.

9. Injection apparatus according to claim 7 wherein said housing includes a cylindrical bore and said valve body is rotatably mounted in said bore.

10. Injection apparatus according to claim 9 wherein said bore includes an end wall and one of said ports is located in said end wall.

11. Injection apparatus according to claim 10 wherein said one port is located on the axis of rotation of said valve body.

12. Injection apparatus according to claim 10 wherein another of said ports is located in the circumferential wall of said bore.

13. Injection apparatus according to claim 12 wherein said passageway includes an axial portion aligned with said one port and a radial portion axially aligned with said other port.

14. Injection apparatus according to claim 13 wherein said radial portion of said passageway and said other port have respectively circular cross sections and flow between said inlet port and said outlet port is permitted upon said radial portion and said other port overlapping.

15. Injection apparatus according to claim 14 wherein said one port is located on the axis of rotation of said valve body.

16. Injection apparatus according to claim 15 wherein said one port is said inlet port.

17. Injection apparatus according to claim 9 wherein said bore includes a circumferential wall extending about said valve body and one of said ports is located in said circumferential wall.

18. Injection apparatus according to claim 17 wherein said passageway includes a radial portion extending to a circumferential wall of said body and axially aligned in said bore with said one port.

19. Injection apparatus according to claim 18 wherein said bore includes an end wall and another of said ports is located in said end wall.

20. Injection apparatus according to claim 19 wherein said passageway includes an axial portion extending from said radial portion to an end face of said body adjacent to said other port.

21. Injection apparatus according to claim 20 wherein said other port and said axial portion are located on the axis of rotation of said valve body.

22. Injection apparatus according to claim 19 wherein a bearing is located between said body and said housing at an opposite end of said bore to said end wall to support said body for rotation in said housing.

23. Injection apparatus according to claim 1 wherein said catheter includes a plurality of spaced apertures at its distal end to permit egress of said contrast agent from an internal duct of said catheter, said distal end being sealed and said apertures being spaced to reduce an initial extent of a bolus of contrast agent in said vessel and to reduce jetting thereof.

24. Injection apparatus according to claim 23 wherein said apertures are spaced apart along the longitudinal axis of said catheter.

25. Injection apparatus according to claim 24 wherein adjacent apertures are displaced circumferentially.

26. Injection apparatus according to claim 25 wherein said apertures provide a cumulative area greater than the cross sectional area of said internal duct.

27. Injection apparatus according to claim 26 wherein said apertures provide a cross sectional area three times that of said internal duct.

28. Injection apparatus according to claim 26 wherein said apertures are arranged as three axially spaced sets and each set includes a pair of diametrically opposed apertures.

29. Injection apparatus according to claim 28 wherein one of said sets is displaced circumferentially 90 degrees from the other two sets.

30. Injection apparatus according to claim 29 wherein said internal duct has an internal diameter of 1 mm and said apertures have a diameter of 0.7 mm.

31. A catheter for use with an injection apparatus to inject a contrast agent into a vessel, said catheter comprising an elongate body having an internal duct extending through said body and sealed at one end to inhibit flow therethrough, a plurality of apertures adjacent said one end of said body to allow egress of said agent from said duct, said apertures being axially spaced from one another along said body with adjacent apertures displaced circumferentially, said apertures being dimensioned to provide a cumulative area greater than the cross sectional area of said internal duct and being located within a 4.7 mm. axial extent of said body whereby an initial extent of a bolus of contrast agent along the vessel is reduced and jetting of the agent is avoided.

32. A catheter according to claim 31 wherein said apertures provide a cross sectional area three times that of said internal duct.

33. A catheter according to claim 32 wherein said apertures are arranged as three axially spaced sets and each set includes a pair of diametrically opposed apertures.

34. A catheter according to claim 33 wherein one of said sets is displaced circumferentially 90 degrees from the other two sets.

35. A catheter according to claim 34 wherein said internal duct has an internal diameter of 1 mm. and said apertures have a diameter of 0.7 mm.

\* \* \* \* \*